United States Patent [19]

Pocock

[11] Patent Number: 5,409,832
[45] Date of Patent: Apr. 25, 1995

[54] MEMBRANE HOLDER FOR USE IN AN ASSAY DEVICE

[75] Inventor: Douglas A. Pocock, Newton, Mass.

[73] Assignee: Stratecon Diagnostics International, Norwell, Mass.

[21] Appl. No.: 177,433

[22] Filed: Jan. 5, 1994

Related U.S. Application Data

[60] Continuation-in-part of Ser. No. 58,496, May 6, 1993, which is a division of Ser. No. 771,830, Oct. 7, 1991, Pat. No. 5,227,290, which is a continuation of Ser. No. 575,132, Aug. 29, 1990, abandoned.

[51] Int. Cl.⁶ ............................................. C12M 1/00
[52] U.S. Cl. ................................. 435/287; 435/970; 435/7.1; 422/56; 422/58; 436/169
[58] Field of Search ............. 422/56, 58, 99, 101, 422/104, 57; 435/7.1, 287, 970; 436/169, 177, 178

[56] References Cited

U.S. PATENT DOCUMENTS

| | | | |
|---|---|---|---|
| 3,809,617 | 5/1974 | Schmitt | 422/56 |
| 4,387,990 | 6/1983 | Yazawa et al. | 356/244 |
| 4,564,503 | 1/1986 | Greisch | 422/58 |
| 4,668,472 | 5/1987 | Sakamoto et al. | 422/58 |
| 4,704,255 | 11/1987 | Jolley | 422/101 |
| 4,777,021 | 10/1988 | Wertz et al. | 422/101 |
| 4,806,487 | 2/1989 | Akers et al. | 436/93 |
| 4,912,034 | 3/1990 | Kalra et al. | 422/58 |
| 4,965,187 | 10/1990 | Tonelli | 435/5 |
| 5,141,719 | 8/1992 | Fernwood et al. | 422/101 |
| 5,147,609 | 9/1992 | Grenner | 422/58 |

Primary Examiner—Robert J. Warden
Assistant Examiner—Theresa A. Trembley
Attorney, Agent, or Firm—Lorusso & Loud

[57] ABSTRACT

A membrane holder for use with a diagnostic device comprises an interlocking first plate and a second plate. The first plate has a top surface flush with a hole, while the bottom surface defines a raised ring, a projection in one corner and an orifice in another corner. The second plate has a top surface having a recess for accepting a membrane, within which is a hole and ribs emanating outwardly to a raised circular rib from which a recessed ring emmanates. The recessed ring of the second plate is adapted to accept the raised ring of the first plate. The top surface of the second plate further has a projection in one corner and an orifice in another corner which mate with those in the first plate. The bottom surface of the second plate has a member to guide liquid away from the membrane. To assemble, a membrane is placed in the recess on the top surface of the second plate. Then, the raised ring on the bottom surface of the first plate is placed over the recessed ring on the top surface of the second plate, and the projection and orifice of the first plate is set to mate with the orifice and projection of the second plate. The plates are then snapped into place, as the orifice and projection each fit within the other, respectively. The raised ring interlocks with the recess, pulling taught the membrane positioned therebetween. Once assembled, the membrane holder may be placed on top of a testing conduit and an assay may be performed on the membrane.

12 Claims, 3 Drawing Sheets

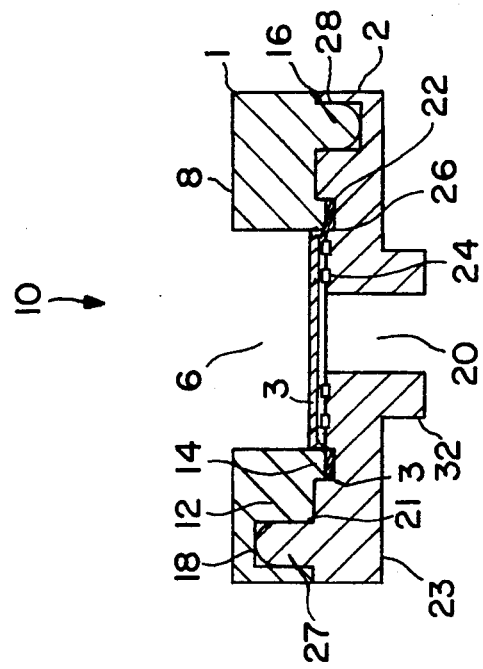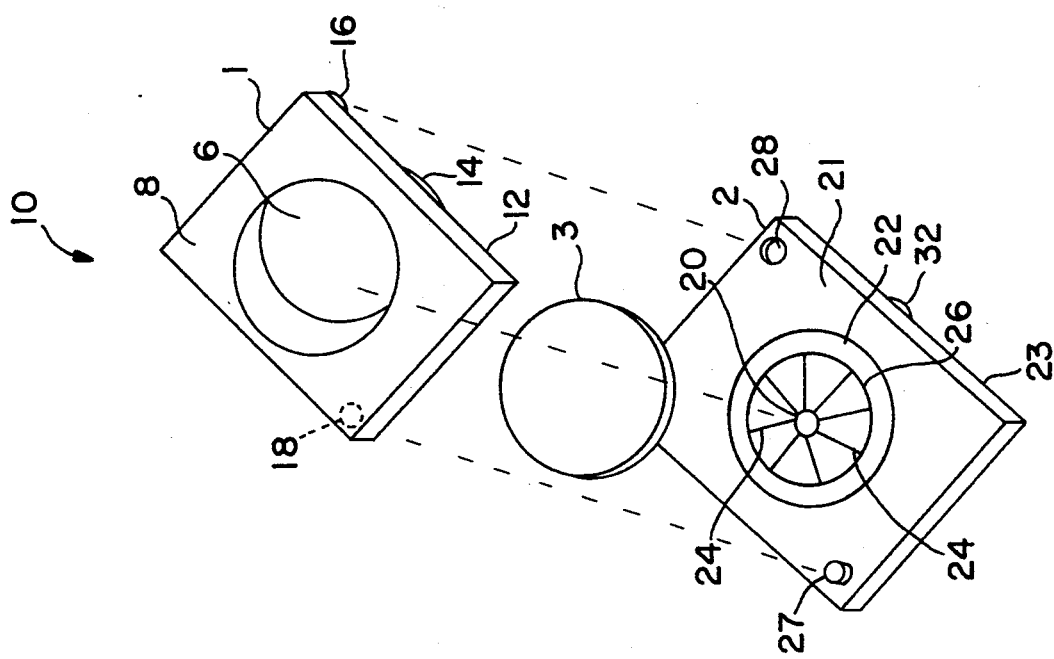

MEMBRANE HOLDER FOR USE IN AN ASSAY DEVICE

This is a continuation-in-part of application Ser. No. 08/058,496 filed on May 6, 1993, which is a divisional of Ser. No. 07/771,83 filed on Oct. 17, 1991, now U.S. Pat. No. 5,227,2 which was a continuation of Ser. No. 07/575,132 filed Aug. 29, 1990, abandoned.

BACKGROUND OF THE INVENTION

1. Field of the Invention

This invention relates to a membrane holder to be used in performing an assay.

Definitions

A membrane includes any organic or inorganic material.

2. Description of the Prior Art

Assays are useful for the quantitation of antigen/-hapten, antibody analyte, or analyte occurring on or attached to cells, or other particulate material, contained in liquid samples of body fluids, such as serum, plasma, urine, or saliva, and non-body fluids, such as cell culture media, potable water, and waste water.

Conventional assay devices include 'wells' which serve as reaction vessels for chemical reactions. Usually, a filter membrane is located at the bottom of each well, and beneath the membrane is a waste reservoir. By applying a vacuum, or a reduced pressure, to the waste reservoir, the liquid undergoing test is drawn through the membrane and into the waste reservoir. As the liquid undergoing test is drawn through the membrane, particulates, or the solid phase, of the liquid is deposited on the membrane. The membrane is exposed to the flowing liquid in a limited area, such that the deposited particulates are concentrated. The deposited particulates may be bacteria, cell fragments, or the like.

The membrane may be provided with antigens, haptens, or their antibodies, to react with a target particulate of the liquid to produce a manifestation of a particular combination, the manifestation often taking the form of producing a certain color. Such "chromogenic" assays may be used for simple and quick tests for various bacteria. A small amount, typically no more than one milliliter, of a liquid is dropped into a "well" drawn by a vacuum bias through a previously prepared membrane and into a waste reservoir. Particulates in the liquid are retained and concentrated by the membrane and react with the immunoreactant with which the membrane has been previously supplied. Given reactions produce differing colors. For example, a positive indication as to presence in the liquid of a target bacteria may be manifested by a purple color, while a negative indication may be manifested by a white color.

There have been many problems associated with the use of membranes in performing multiple and varied assays. Most conventional assay devices employ one membrane to serve multiple wells. The use of a single membrane in such a manner inevitably leads to crosstalk between wells due to the ability of liquid to disperse on the membrane. Crosstalk between wells leads to inaccuracies in test results and often misdiagnosis of illness. Notwithstanding the danger of crosstalk, such devices are limited in their effectiveness in performing different types of assays. The membrane used in performing an assay is dependent on the type of assay being performed, different assays requiring different membranes.

Most conventional assay devices come prefabricated, as the membrane is ultrasonically welded, bonded or screwed to a holder at the manufacturing facility. Should an operator wish to perform a test requiring a membrane other than that provided, he/she is forced to order a new device or holder, or risk destruction of the device in attempting membrane substitution.

One example of such a device is disclosed in U.S. Pat. No. 4,704,255, issued Nov. 3, 1987 to Jolley. This device includes a large number of wells all served by a single membrane and a single waste reservoir. The membrane is joined to a one of the welded plates forming the assembly, by placing it into a mold for the plate, prior to injection molding of such plate.

A similar device is disclosed in U.S. Pat. No. 5,141,179 to Fernwood et al. Disclosed is a multiple well assay device. A multi-plate assembly constructed with screws for fastening the plates to the wells, the membrane is also firmly attached in such a process by the manufacturer. Although this device may if desired, be constructed with one membrane per well, the membrane and the well are fixed and not interchangeable by the operator.

Similarly, U.S. Pat. No. 4,387,990 to Yazawa et al. teaches a single well construction thus admitting only one membrane per assay. This device is comprised of two or three plates, one of such having a recess for accepting a membrane. However, like the above devices, the membrane is fixed, as after the membrane has been placed in the recess, a process of bonding the plates which hold the membrane, is carried out at a manufacturing facility.

Yet another single test membrane holder is disclosed in U.S. Pat. No. 4,965,187 to Tonelli. This device comprises a molded cup member with a filter therein, adapted to fit over a membrane holder. The membrane holder comprises a disc upon which the membrane sits. The membrane, however is glued to the holder, thus discouraging removal for substitution with another membrane.

Although the above device provides secure a membrane on a holder, such pre-prepared assemblies are not flexible enough to permit the operator to customize or design his own tests. Although they are available for widely used tests, they may not be available for lesser known tests or for tests being developed in the laboratory, requiring differing membranes. Additionally with such pre-prepared membranes, the attachment of such on a holder during manufacture is often uneven or bunched. The potential for unevenly set membranes to yield incorrect results is high.

One device permitting free placement of a membrane in a membrane holder is disclosed in U.S. Pat. No. 4,806,487 to Akers et al. This device is comprised of a perforated support member upon which a cellulosic disk lies. However, such a device does not provide for secure placement of the disk, as the disk sits in place only due to the force of gravity. This likelihood of the disk moving or becoming dislocated from the device is great. This could be potentially life threatening should the disk be used for testing the presence of an infectious disease. Moreover, this disk is large and used in a device which only permits one test to be carried out at a time. Moreover if another test is desired, the operator must wash out the funnel and place another disk therein, a cumbersome and potentially unhealthy job.

SUMMARY OF THE INVENTION

It is, therefore, an object of the present invention to provide a process for preparing the membrane and inserting the membrane into the assay device that is simple enough to be performed by the operator in the laboratory.

It is another object of the invention to enhance the surface characteristics of the membrane upon which an assay can be performed.

It is another object of the invention to effect controlled dispersion of liquids on such a surface during testing.

It is another object of this invention to allow the operator to prepare a wide variety of membrane assemblies without having to order pre-prepared membranes.

It is still another object of the present invention to provide the operator with the ability to design his own tests and immediately put them into operation.

It is yet another object of the present invention to eliminate the delay involved when an operator is required to order pre-prepared membrane assemblies in advance of their use.

It is still another object of the present invention to prevent the operator from coming into contact with the potentially infectious matter being assayed.

With the above and other objects in view, as will hereinafter appear, the present invention provides a novel apparatus and method for forming a membrane holder for use in an assay device. The membrane holder of the instant invention comprises a first plate and a second plate between which a membrane is locked into place. The first plate has a top surface flush with a central hole, while the bottom surface defines a raised ring. The bottom surface further has a projection in one corner thereof, and an orifice in another corner thereof.

The second plate, adapted to lock with the first plate has a top surface with a recess and a hole therein, the recess accepting a membrane. Within the recess are ribs emanating outwardly from the center of the hole, extending to a raised circular rib from which a recessed ring emmanates. The recessed ring is adapted to accept the raised ring of the first plate upon assembly. The top surface further has a projection in one corner thereof, and an orifice in another corner thereof, in exactly the opposite corners of the first plate's bottom surface so as to mate therewith. The bottom surface of the second plate, further has an outlet member to guide liquid away from the membrane holder during testing.

To assemble, a membrane is placed in the recess on the top surface of the second plate. Then, the raised ring is placed over the recessed ring, and the projection and orifice of the first plate is set to mate with the orifice and projection of the second plate. The plates are then snapped into place, as the orifice and projection each fit within the other, respectively. The raised ring interlocks with the recess, pulling taught the membrane positioned therebetween. Once assembled, the membrane holder is placed on top of a testing conduit and dropped evenly therein. A dowel is then used to push the membrane holder into the well until it rests upon a membrane holder support. The above steps are repeated for each well.

The membrane is sized for the holder through a process whereby the operator uses an easily manipulable cutter to cut a portion of a membrane material and transport the cut portion of the membrane to a membrane holder. The cutter is adapted to retain the cut membrane until a release button on the cutter is activated. This enables the operator to cut the membrane and deposit it in the membrane holder without ever having to touch it. When the release button is activated, the membrane material is placed on a bottom plate of the membrane holder.

The instant invention provides greater flexibility in the laboratory by providing a method whereby a user prepares his/her own membrane holder assemblies. By preparing his/her own membrane assemblies a variety of different tests may be carried out without having to order them in advance. For example, an operator might elect to use a nylon membrane in one test conduit and nitrocellulose or cellulose acetate membrane in another conduit; or an operator may elect to use the same, or similar materials, but having different weaves; or may elect to compare results of membranes of different manufacturing sources. Moreover, the structure of the assembly of the instant invention guarantees even dispersion of test material and reagent during testing. This feature is important in providing effective test results.

The above and other features of the invention will now be more particularly described with reference to the accompanying drawing and pointed out in the claims. It will be understood that the particular devices and methods embodying the invention are shown by way of illustration only and not as limitations of the invention. The principles and features of this invention may be employed in various and numerous embodiments without departing from the scope of the invention.

BRIEF DESCRIPTION OF THE DRAWINGS

FIG. 1 is an exploded view of the membrane holder with membrane.

FIG. 2 shows a cross sectional view of the membrane holder, upon assembly by the operator.

DETAILED DESCRIPTION OF THE PREFERRED EMBODIMENT

Figure 3:
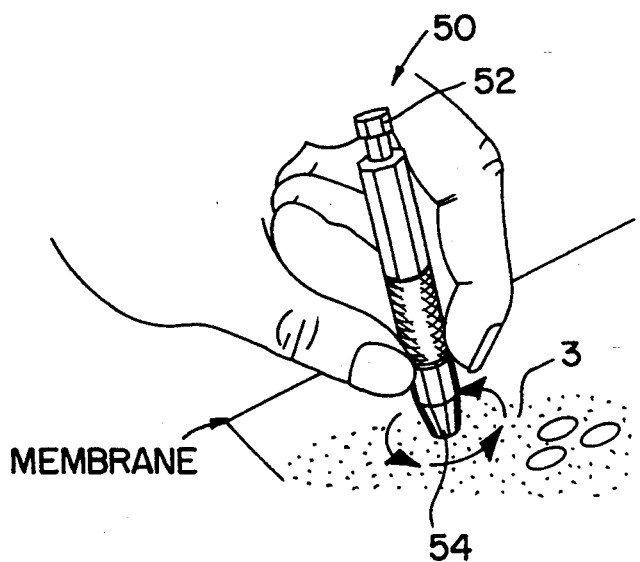
FIG. 3 shows the cutter as it is used to cut the membrane.

FIG. 1 shows an exploded view of the membrane holder 10 of the instant invention. The membrane holder 10 is comprised of a first plate 1 and a second plate 2, both of which are adapted to tautly secure a membrane 3 therebetween.

The first plate 1 is comprised of a solid member of a certain thickness, defining a hole 6 therethrough. This hole as will be shown in FIG. 2 forms a testing well. The top surface 8 of the first plate 1 lies flush with the hole 6, while the bottom surface 12 of the first plate 1 has a raised ring 14 defining the periphery of the hole 6. Additionally formed in two corners of the bottom surface is a raised projection 16 and an orifice 18, respectively for joining the first plate 1 with the second plate 2.

The second plate 2 is comprised of a solid member of a certain thickness, also having a hole 20 therethrough.

The hole 20 in the second plate 2 is shown as being of a lesser diameter than that of the first plate 1, however the diameter need not be so limited. The top surface 21 of the second plate 2 has a central recess 22 which leads inwardly to the hole 20, adapted to accept a membrane 3. Furthermore, within the recess 22 are ribs 24 emanating outwardly from the center of the hole 20. The ribs extend to a recessed ring 26. This recessed ring 26 is adapted to accept the raised ring 14 of the first plate 1. The top surface 21 further has a projection 27 in one corner thereof, and an orifice 28 in another corner thereof, in cooperating corners as in the first plate's 1 bottom surface 12. The bottom surface 23 of the second plate 2, further has an outlet member 32 adapted to guide liquid away from the membrane holder 10 during testing.

A cross section of the membrane holder after it has been assembled is shown in FIG. 2. The user easily assembles the membrane holder 10, by placing a membrane 3 in the recess 22 of the second plate 2. The first plate 1 is then placed over the second plate 2, with the projection 16 and orifice 18 in the bottom surface 12 of the first plate 1 contacting the orifice 28 and projection 27 in the top surface 21 of the second plate 2. A gentle push on the first plate 1 causes it to snap in place with the second plate 2 with through the action of the raised ring 14 fitting within the recess ring 26 and the orifices 18, 28 mating with projections 16, 27. The raised ring 14 and recessed ring 26 function to tautly secure the membrane thus yielding a membrane with even surface contours. The first plate 1 thus having a certain thickness forms a well in which the membrane 3 forms the floor.

The invention contemplates the use of any membrane 3 provided with antigens, haptens, or their antibodies, to react with a target particulate of the liquid undergoing the test to produce a manifestation of a particular combination, the manifestation often resulting in the production of a certain color. The membrane 3 may be coated with the antigens, haptens, or their antibodies prior to being cut, or the reagents may be added to the membrane after the membrane holder 10 is in place in the well.

Figure 4:
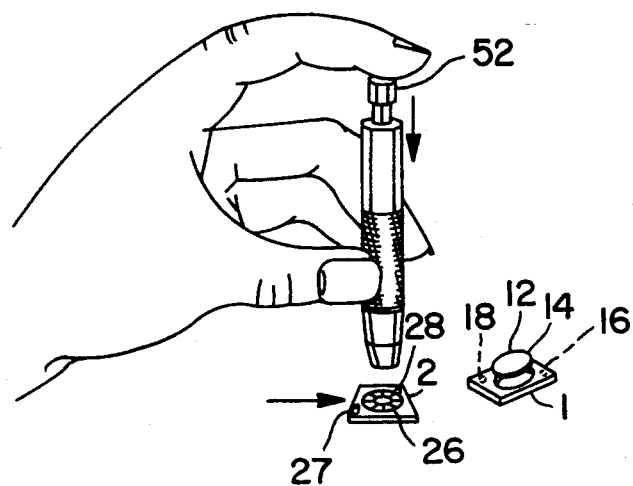
FIG. 4 shows the cutter as the release button is activated.
Figure 5:
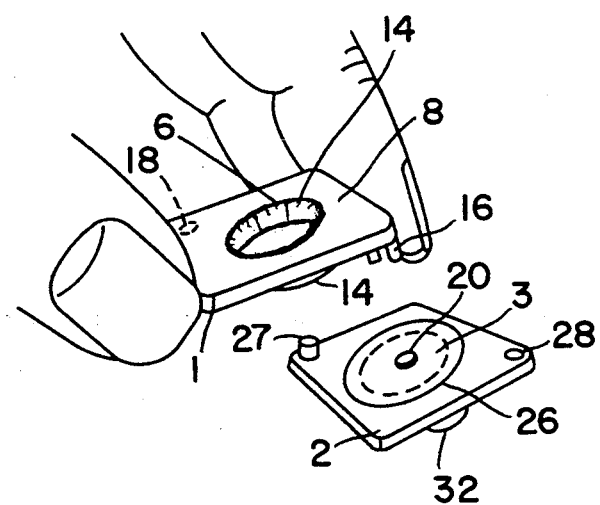
FIG. 5 is a perspective view of a membrane holder.

Referring to FIGS. 3-5, the method of forming the membrane and membrane holder is shown. As given in FIG. 3, a membrane material 3 is laid on a flat surface. The membrane 3 may be treated with the antigens, haptens, or their antibodies at this stage, or at a later stage. A cutter 50 is used to cut the membrane 3 and transport the cut portion to the membrane holder 10. The cutter 50 has a cutting end 54 at one end and a release button 52 at the opposite end. The cutting end 54 is adapted to cut the membrane 3 and retain it until the release button 52 is activated. In this manner, the membrane 3 may be cut and transported without ever having to touch the human hand. This is especially important because it prevents foreign substances from touching the membrane 3 which might interfere with the test results. In order to cut the membrane 3, the cutter 50 is placed on the membrane 3 material with the cutting end 54 in contact with the membrane material. It is twisted and lifted, and the cut portion of the membrane 3 is retained in the cutter.

After cutting, the cutter 50 is then positioned over the second plate 2 of the membrane holder 10 and the release button 52 is activated, as shown in FIG. 4. The membrane 3 is then deposited onto the recess 22 of the second plate 2 of the membrane holder 10.

As shown in FIG. 5, assembly is then carried out very easily. With the membrane 3 in place on the second plate 2, the first and second plates 1, 2 are locked together by the interfitting projections 16, 27 and orifices 18, 28, or the like, adapted to "snap" into essentially a permanent lock, with the membrane 3 disposed within the recess 22 of the second plate 2, between the hole 6, 20.

Figure 8:
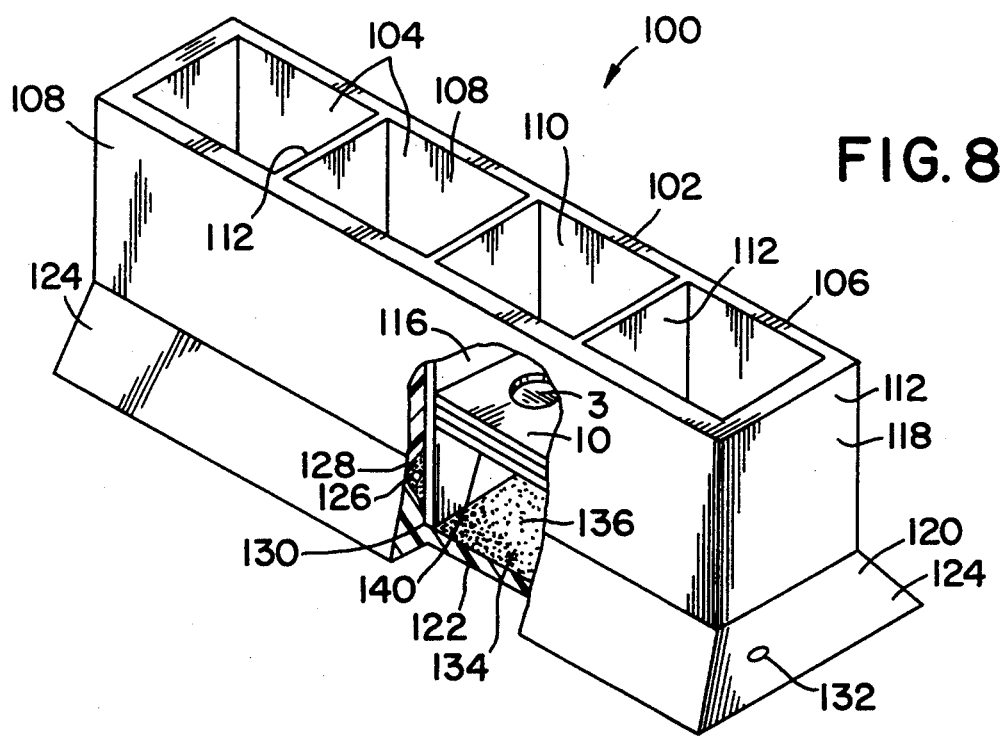
FIG. 8 is a perspective view of the membrane holder with membrane used in a diagnostic device.

FIG. 8 shows a typical diagnostic device 100 in which the membrane holder is to be used. It includes a first housing 102 having a plurality of openings 104 in a top surface 106 thereof. The openings 104 are defined by wall means 108 depending from the top surface 106. The wall means 108 define conduits 110 which extend from the top surface 106 through the first housing 102.

The wall means 108 include barrier walls 112 disposed between each adjoining two of the conduits 110. In the assembled version, the membrane holder 10 (not shown) are disposed in each of the conduits 110 and are adapted to permit flow of a liquid under test therethrough, as will be further described hereinbelow. The barrier walls 112 extend beyond a bottom plane 116 of the first housing 102.

The diagnostic device 100 further includes a second housing 120, which comprises a reservoir portion, having a bottom wall 122 and upstanding side walls 124. The lower edge 128 of the first housing 102 is fixed to the surface 126 of the second housing side wall 124, as by ultrasonic welding, to form a combined housing. A distal edge 130 of each of the barrier walls 112 extends to a point proximate the bottom wall 122.

The second housing side wall 124 is provided with a port 132 by which pressure is reduced in the second housing, and thereby in the lower regions of the conduits 110, to draw flow of liquid material, after introduction into the conduits 110 through the openings 104, through the conduits and through the membrane holder 10.

The bottom wall 122 of the second housing 120 is covered, wholly or in part, with a layer of absorbent material 134 before joining of the first and second housings 102, 120. Upon joining of the housings 102, 120, the distal edges 130 of the barrier walls 112 are disposed adjacent the absorbent material 134. The presence of the absorbent material 134 and the barrier walls 112 greatly reduces the possibility of liquid having passed through one conduit and membrane reaching a neighboring membrane. The absorbent material 134 tends to absorb liquid droppings from an membrane holder 10 and if, because of the quantity of liquid involved, there is a splash off the bottom wall of the second housing 120, the barrier walls 112 operate to stop the flight of errant droplets before they reach an adjoining conduit. The first housing barrier walls 112 and the second housing side walls 124 form a reservoir chamber 136 at a lower end of each conduit 110, into which tested liquid drops from the membrane holder 10. The absorbent material 134 and the barrier walls 112 operate to confine such liquid to its respective chamber 136. Each of the conduits 110 is provided with a support means 140 for supporting the membrane holder. The diagnostic device is connected to the a vacuum apparatus or source of reduced pressure through port 132.

The operator may then introduce a liquid to be tested into one of the conduits 110, The liquid is drawn through the membrane 3, leaving particulates, in concentrated fashion, on the membrane 3 for reaction with enzymes, or the like, with which the membrane previously has been prepared. The liquid then drops into the reservoir chamber 136 of its conduit 110 and is absorbed by the material 134, preventing its evacuation through the vacuum port 132 and luer not shown.

Figure 6:
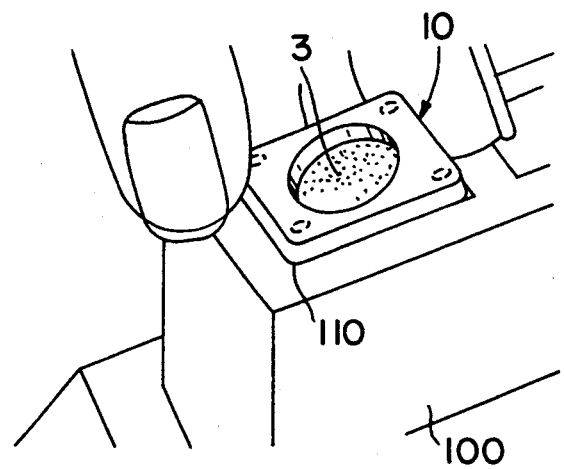
FIG. 6 shows the membrane holder as it is positioned in a test well of the diagnostic device.
Figure 7:
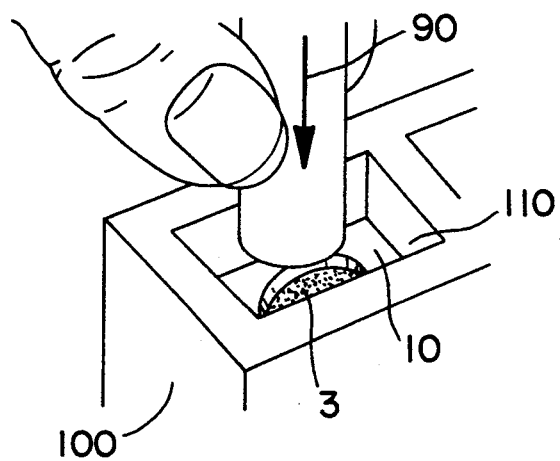
FIG. 7 shows a snapper dowel as it is used to push the assay means into the well of the diagnostic device.

In positioning the membrane holder in diagnostic device we return to FIGS. 6 and 7. The membrane 3 assembled within the membrane holder 10 lies taut due to the action of the ring 14 and recess ring 26. As shown in FIG. 6, the membrane 3 within the membrane holder 10, it then positioned flatly over a conduit 110 and dropped evenly into it. As shown in FIG. 7, a snapper dowel 90 may also be used to push the membrane holder 10 into the conduit 110 until it rests on the support member inside the conduit 110. The membrane holder 10 provides the operator with the ability to use membranes of different characteristics for forming different tests in different conduits, for comparison. For example, an operator might elect to use a nylon membrane in one test conduit and a nitrocellulose or cellulose acetate membrane in another conduit; or an operator may elect to use the same, or similar materials, but having different weaves; or may elect to compare results of membranes of different manufacturing sources.

In view of the many safeguards disposed around the individual membrane means and the isolation of the reservoir chambers, along with the absorbent material disposed in the reservoir chamber, there is little likelihood of migration or "cross-talk" from one conduit to another, insuring that no test is carried out on a membrane material contaminated by a previous test.

The instant invention provides the operator with a membrane holder which is easily assembled with which he can employ any membrane desired. The plates, inexpensive and easily manufactured, revolutionize conventional processes whereby membrane holders are manufactured with expensive ultrasonic welding devices and the like. Moreover, the diagnostic assay device in which the membrane holder is adapted for use, further provides the enhanced feature of preventing operator contact with potentially threatening diseases.

It is to be understood that the present invention is by no means limited to the particular constructions or procedures herein disclosed and/or shown in the drawings, but also comprises any modification or equivalents within the scope of the claims.

Having thus described my invention, what I claim as new and desire to secure by Letters Patent of the United States is:

1. A device for holding a membrane comprising:
   a first plate having a top surface and a bottom surface, and a central hole defined therein, extending from said top surface to said bottom surface, said bottom surface comprising a raised ring encircling said central hole,
   a second plate having a top surface and a bottom surface, and a central hole defined therein, extending from said top surface to said bottom surface, said top surface comprising; a recessed ring capable of receiving said raised ring, and a plurality of ribs extending outwardly from said central hole and terminating at said recessed ring,
   a membrane capable of lying on said plurality of ribs on said top surface of said second plate, whereupon joining of said first plate and said second plate via a snap-fit assembly of said raised ring of said first plate with said recessed ring of said second plate, secures said membrane tautly on said top surface of said second plate, thus yielding a membrane having even surface contours.

2. A device for holding a membrane according to claim 1, wherein said central hole of said first plate and said central hole of said second plate are alligned upon joining of said first plate and said second plate, so as to expose a portion of said membrane.

3. A device for holding a membrane according to claim 1, wherein said first plate further comprises at least one projection and at least one orifice and said second plate further comprises at least one projection and at least one orifice.

4. A device for holding a membrane according to claim 3, whereby said at least one projection on said first plate mates with said at least one orifice on said second plate.

5. A device for holding a membrane according to claim 3, whereby said at least one orifice on said first plate mates with said at least one projection on said second plate.

6. A device for holding a membrane according to claim 1, wherein said ribs effect even displacement of fluid on said membrane.

7. A device for holding a membrane comprising;
   a first plate having a raised ring, said first plate defining an opening therethrough, said first plate further having at least one projection thereon,
   a second plate having a plurality of radiating ribs and a recessed ring formed therein, said second plate defining an opening therethrough, said second plate having at least one orifice therein, said first plate and said second plate being joined by a mating of said projection and said orifice, said second plate locking a membrane in place with said first plate via a snap-fit assembly of said raised ring and said recessed ring, thereby securing a membrane over said radiating ribs, said membrane being exposed between said first plate and said second plate by said opening in said first plate and said opening in said second plate, such that an assay can be performed thereon.

8. A device for holding a membrane according to claim 7, said snap-fit assembly tautly securing said membrane, such that said membrane surface has an even contour.

9. A combination membrane holder and diagnostic device comprising;
   a membrane holder comprising:
   a first plate having a raised ring defining an opening in said first plate, said first plate further having means for attaching,
   a second plate having a plurality of radiating ribs and a recessed ring formed therein, said recessed ring defining an opening in said second plate, said second plate further having means for attaching,
   a membrane fixed tautly between said first plate and said second plate via a snap-fit assembly of said raised ring and said recessed ring, said membrane exposed by said opening in said first plate and said opening in said second plate,
   a diagnostic device capable of receiving said membrane holder comprising:
      a housing having at least one conduit formed therein, said at least one conduit sized to accommodate said membrane holder, and collection means for receiving assaying matter transmitted through said conduit and membrane in said membrane holder.

10. A method of assembling a membrane in a membrane holder comprising the steps of:

provinding a first plate having a raised ring defining an opening in said first plate, providing a second plate having a plurality of radiating ribs encircled by a recessed ring, said recessed ring defining an opening in said second plate, placing a membrane onto said second plate, covering said radiating ribs, positioning said first plate over said second plate so as to cover a portion of said membrane, locking the first plate and the second plate to form a membrane holder, by snap-fitting said raised ring into said recessed ring, tautly securing said membrane in said membrane holder so that said membrane has an even-contoured surface.

11. The method of claim 10 further comprising the step of:

positioning the membrane holder over a conduit formed in an assay device and dropping it evenly into the conduit.

12. The method of claim 11 further comprising the steps of:

placing matter to be assayed into said conduit such that it rests on said membrane, performing an assay on said membrane, repeating the above steps with a fresh first plate, a fresh second plate, a fresh membrane and a fresh conduit.

* * * * *